(12) United States Patent
Lupton

(10) Patent No.: US 7,172,618 B2
(45) Date of Patent: Feb. 6, 2007

(54) CATHETER AND STENT

(75) Inventor: Henry William Lupton, Surrey (GB)

(73) Assignee: Abbott Laboratories, Abbott Park, IL (US)

( * ) Notice: Subject to any disclaimer, the term of this patent is extended or adjusted under 35 U.S.C. 154(b) by 280 days.

(21) Appl. No.: 10/076,369

(22) Filed: Feb. 19, 2002

(65) Prior Publication Data

US 2003/0114911 A1 Jun. 19, 2003

(30) Foreign Application Priority Data

Feb. 19, 2001 (GB) ................... 0104069.0

(51) Int. Cl.
*A61F 2/06* (2006.01)
(52) U.S. Cl. .................................... 623/1.11
(58) Field of Classification Search ............... 623/1.11; 606/194–195, 108
See application file for complete search history.

(56) References Cited

U.S. PATENT DOCUMENTS

| 4,998,923 | A | * | 3/1991 | Samson et al. ............. 606/194 |
| 5,147,315 | A | * | 9/1992 | Weber ................... 604/164.09 |
| 5,968,069 | A | * | 10/1999 | Dusbabek et al. .......... 606/194 |
| 6,503,353 | B1 | * | 1/2003 | Peterson et al. ............... 156/86 |
| 6,607,551 | B1 | * | 8/2003 | Sullivan et al. ............ 623/1.11 |

* cited by examiner

*Primary Examiner*—(Jackie) Tan-Uyen T. Ho
(74) *Attorney, Agent, or Firm*—Sughrue Mion, PLLC

(57) ABSTRACT

A catheter and stent combination for insertion into the lumen of a human or animal body. The catheter has an elongate body with proximal and distal ends, the body comprising a hollow tubular member. At least one section of the walls of the tubular member in the distal region is corrugated and the stent is positioned thereover.

6 Claims, 5 Drawing Sheets

CATHETER AND STENT

This invention relates to catheters and stents for insertion into the lumen of a human or animal body. The invention in particular relates to balloon catheters of the type used for the delivery of medical devices such as stents.

Catheters are usually inserted into a body lumen over a guidewire and into a position in which a treatment can be performed or a device placed on the catheter can be delivered. Because of the need for the catheter to pass through narrow lumens there are severe restrictions in terms of maximum catheter diameter. Also because such catheters must be lengthy they need to be formed from resilient material that is resistant to unwanted axial twisting whilst still being extremely flexible so that they can pass through the curves of a body lumen. This applies considerable constraints in terms of the materials that may be employed in catheter construction. It also constrains the ability to provide appropriate rigidity in the catheter if a hollow lumen catheter is necessary and also makes it difficult to provide appropriate support for stent placed therein to be delivered. This is a particular problem at the catheter tip, where it may be necessary to provide an expansion balloon as well as support for the stent, resulting in a region which is built up with respect to the remainder of the catheter yet for which it would still be desirable to provide appropriate flexibility to enable good manoeuverability for the catheter as a whole. For example, catheters are known for which an expansion balloon is provided toward their distal end, the expansion balloon supporting a stent which is deployed by expansion of the balloon once the balloon region has been placed in the desired position in a body. So that the stent can be retained properly until deployment such catheters often require a built-up region underneath the balloon and the stent so that the stent is held on the catheter with sufficient retention force. Regardless of the material from which the built-up region is made, this results in a thickening of the tip region of the catheter and naturally stiffens any support lumen beneath the built-up region.

The present invention seeks to provide a catheter with a more flexible tip that overcomes some of the above problems.

According to the present invention there is provided a catheter and stent combination for insertion into the lumen of a human or animal body, the combination comprising:

a catheter having an elongate body with proximal and distal ends, the body comprising a hollow tubular member, wherein at least one section of the walls of the tubular member in the distal region is corrugated; and a stent wherein a support region is formed over the corrugated section in order to provide supporting retention for a stent placed there over in use.

The corrugation may be provided by a series of circular indentations forming ribs therebetween. Alternatively, the corrugation may be provided by a single spiral indentation along the wall. If a series of circular indentations are provided then slots may be cut in the ribs that are formed to provide additional flexibility in the corrugations.

Wire may be inserted into the corrugated section to provide a region of increased radiopacity.

The corrugated section may have a balloon formed over it.

The corrugated section of the catheter of the present invention has flexibility to a section of a catheter which is usually rigid with respect to other portions of the body of the catheter. It does this while still retaining rigidity to reduce the likelihood of unwanted kinking in the tubular body of the catheter. However, it still provides the ability for additional support structures and a balloon configuration to be provided over it so that the overall functionality and retention characteristics of the catheter can be retained.

Examples of the present invention will now be described with reference to the accompanying drawings, in which.

Figure 5:
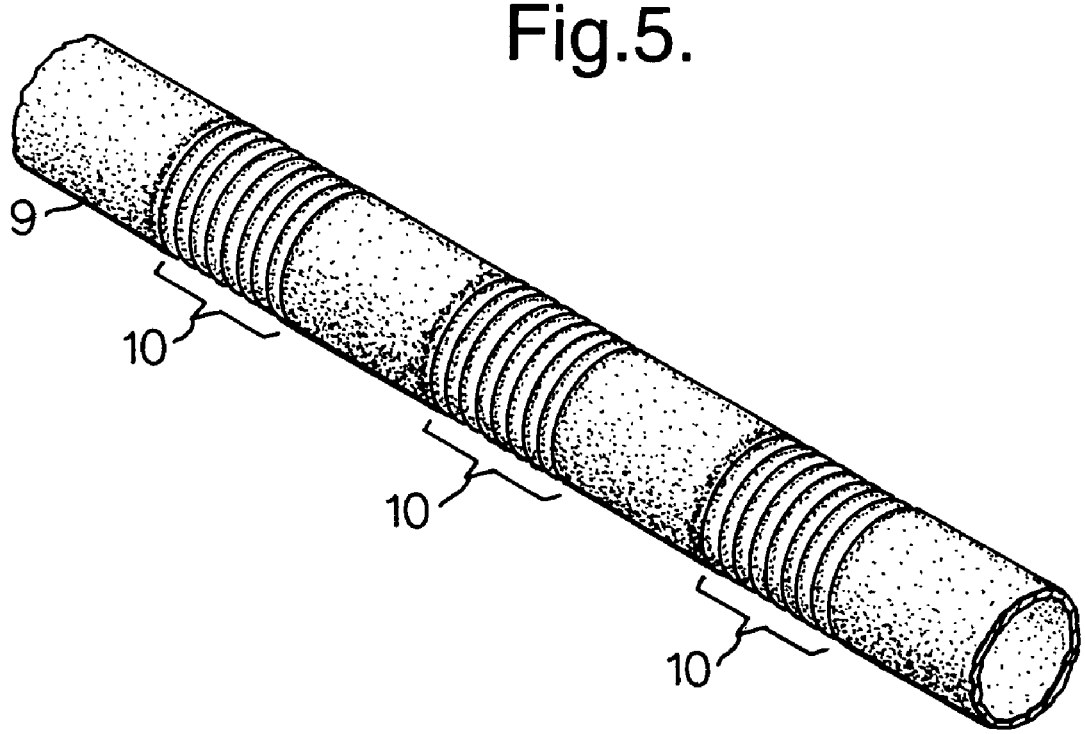
Figure 6:
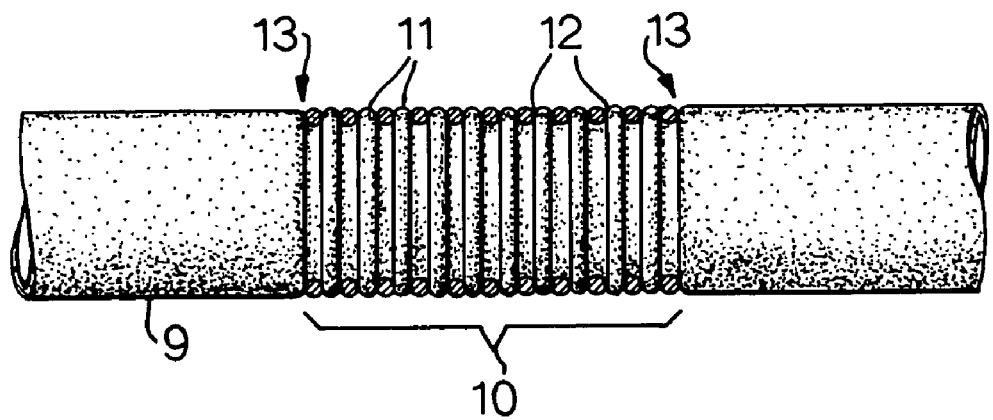

FIGS. 4*a* to 4*g* show alternative example corrugation configurations that may be employed in the present invention;

FIG. 5 shows a further example of a corrugation section in accordance with the present invention; and FIG. 6 shows an example of the present invention with radiopaque wire inserted therein.

Figure 1:
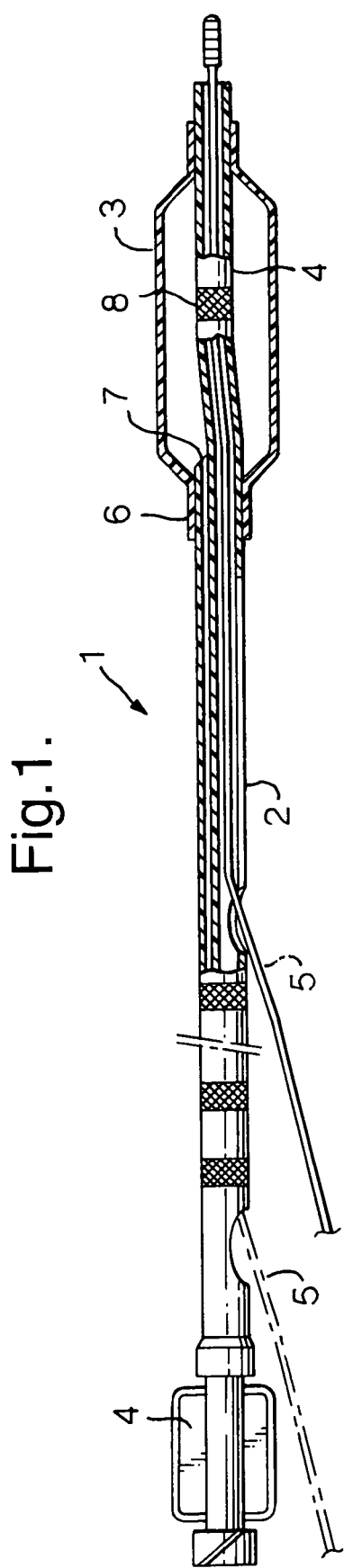
FIG. 1 is a schematic partial cross-sectional view of a prior art catheter.

Referring to FIG. 1, a known catheter 1 has a main body 2 with a distal end 3 and a proximal end 4. In use, the catheter 1 is guided over a guidewire 5 so that the distal end 3 can be positioned in a desired location within a body lumen (not shown). The prior art catheter 1 that is shown is of the balloon type and has a balloon 6 at the distal end 3 which can be inflated in use by the pumping of fluid (not shown) from the proximal end 4 via a lumen 7 which opens in the balloon 6. The distal region 3 has a support structure 8 formed on the tubular member 9 which forms the main body of the catheter 1 of which surrounds the guidewire 5 in use. The support section 8, shown only partially in FIG. 1, provides a raised region when the balloon 6 is compressed over it so that a stent (not shown) positioned over the balloon 6 can be retained on the catheter 1 without fear of it falling off and without damage to the stent when it is compressed onto the balloon 6.

Figure 2:
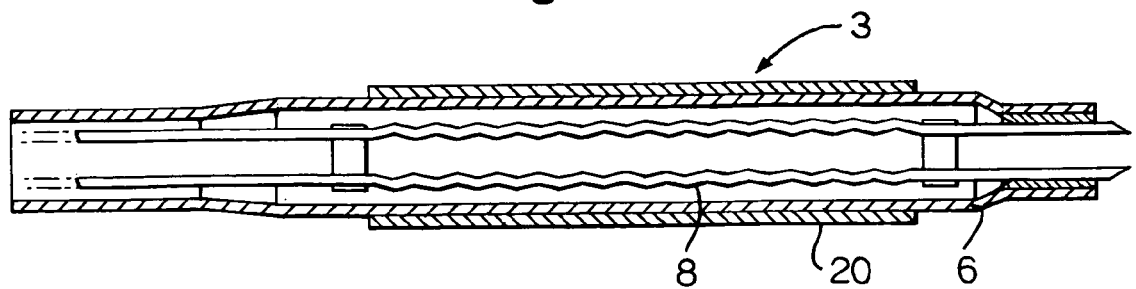
FIG. 2 is a side cross-sectional view of a tip of a stent and catheter combination according to the invention.

FIG. 2 shows a cross-sectional view of the tip of a catheter according to the invention with a stent 20 placed thereover. In this figure, components that correspond to those of the prior art catheter of FIG. 1 are numbered identically. As can be seen from this figure, the stent 20 is positioned over an expandable balloon 6 which, in use, can be inflated to expand the stent 20 to deliver it to a desired position in a body lumen. As will be appreciated, if the stent 20 is of the self-expanding type then the balloon portion of the catheter and stent combination may not be required. The catheter of FIG. 2 has a support section 8 which may be hollow to allow a guide wire (not shown) to pass therethrough in use. The support section 8 is shown, for ease of understanding, out of contact with the balloon 6, but in practice the two would be in engagement in order to ensure as small a cross-sectional profile for the catheter and stent arrangement as is possible. As can be seen from FIG. 2, the support section 8 is corrugated. The corrugations may or may not extend along the full length of the stent 20, but provide a level of flexibility for the distal region 3 that is not possible in the prior art configuration shown in FIG. 1. However, because of the raised ribs of the corrugated section, there is no loss in the gripping force that can be provided to the stent 20.

Figure 3A:
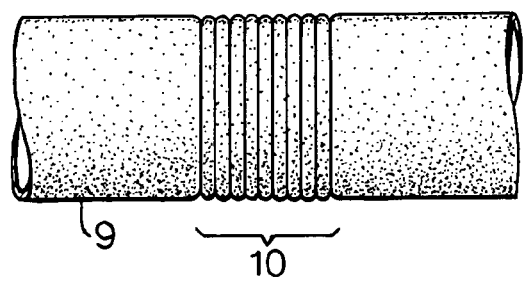
FIG. 3 is a schematic side view of a corrugated section in an example catheter according to the invention both in a compressed and a stretched state.
Figure 3B:
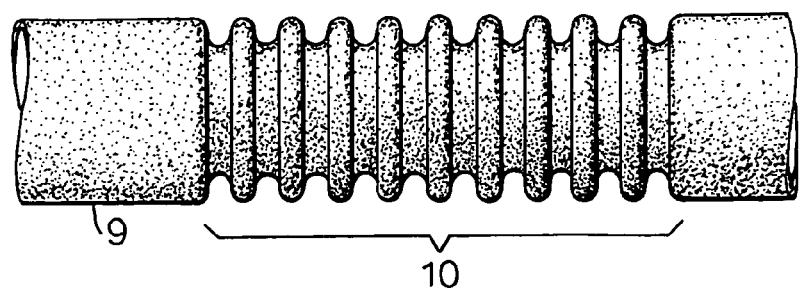

FIG. 3 shows a portion of a catheter according to the present invention. Components which correspond to those shown in the prior art catheter of FIG. 1 and the example catheter of FIG. 2 are numbered identically.

The two examples shown in FIG. 3 show a tubular member 9 from the distal portion of a catheter according to the present invention which may be of the balloon type shown in FIG. 2 and which is configured in combination with a stent to deliver the stent. The tubular member 9 has a corrugated section 10 which can be compressed and stretched as shown in figure. It will be appreciated that the corrugated section 10 provides resistance to kinking but increases the flexibility of the tubular member 9 when it is bent so that its axis is not straight. FIGS. 4a to 4g show examples of corrugation types that may be provided with the present invention. FIGS. 4a to 4d show ribs 11 which vary in number and thickness in the axial direction and which define slots 12 which are also of varying width and thickness in the axial direction. The example corrugated section 10 of FIG. 4a has ribs 11 which stand proud of the outer diameter of the tubular member 9 to provide a support region similar of function to that of support region 8 shown in FIGS. 1 and 2. The relative thicknesses of the ribs 11 and slots 12 can be chosen dependent upon the level of flexibility and kink-resistance that is required, as well as the level of retaining force that may be required to be applied to a stent positioned thereover in use.

Figure 4A:
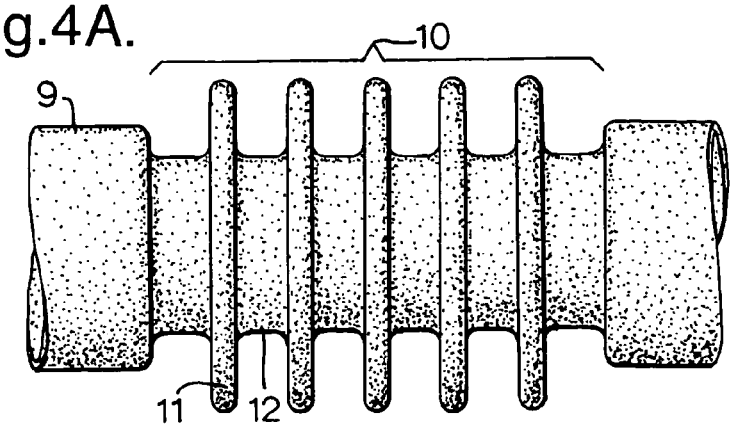
Figure 4B:
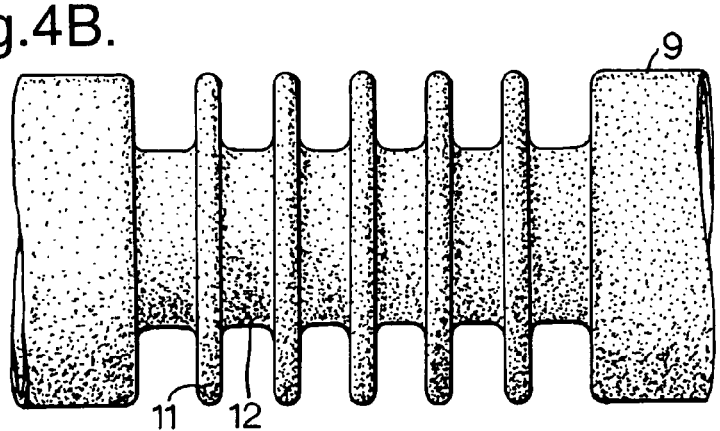
Figure 4C:
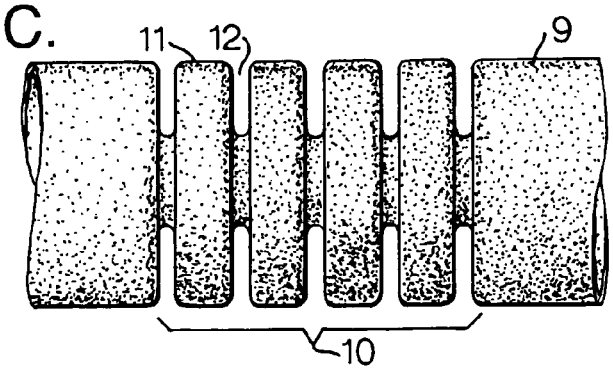
Figure 4D:
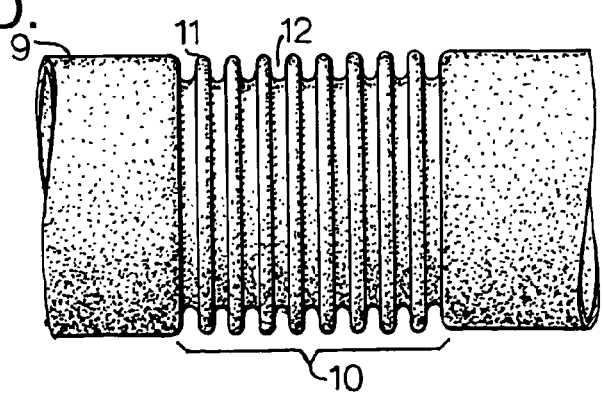
Figure 4E:
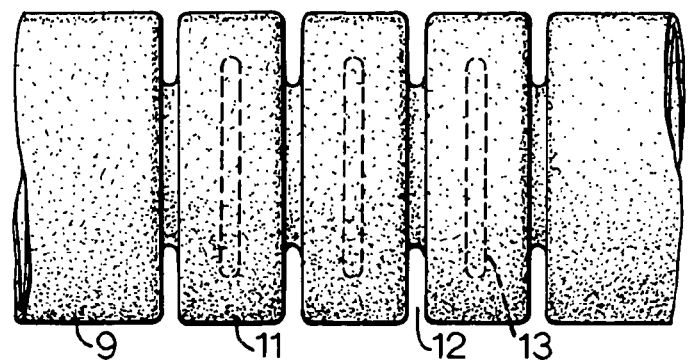
Figure 4F:
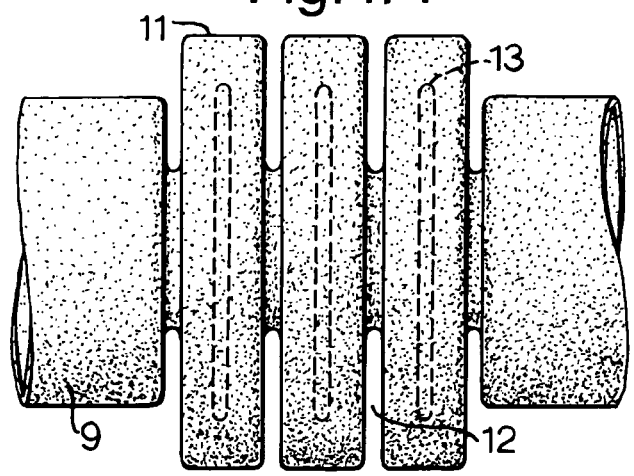
Figure 4G:
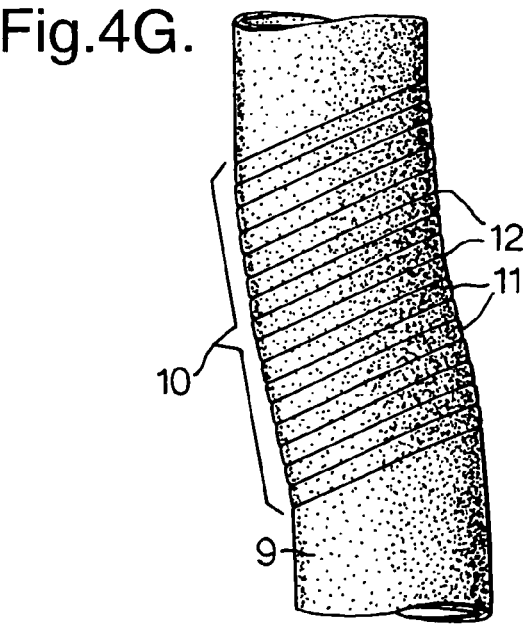

FIGS. 4e and 4f show alternative configuration which again have ribs 11 and slots 12, but which have additional slots 13 cut within at least some of the ribs 11 to provide additional flexibility and also to provide the strain relief during flexing of the tubular member 9. The example of FIG. 4f again has ribs 11 which are proud of the outer diameter of the tubular member 9.

The example of FIG. 4g again has a corrugated region 10 which is formed from a single spiral rib 11 which defines a spiral slot 12. This example may be adapted such that the rib 11 stands proud of the outer diameter of the tubular member 9 as with other examples.

FIG. 5 shows a further example of the invention in which plural corrugated sections 10 are provided. In this example any of the configurations shown in FIGS. 3 and 4 may be employed for each of the corrugated sections 10 and may be mixed to provide optimum flexibility and retaining force as required.

FIG. 6 shows a further example of the present invention in which the corrugated section 10 has radiopaque filaments 13 embedded therein. These may be embedded either in the ribs 11 or the slots 12. Again, the corrugated section 10 may be of the construction of any of the preceding examples. The present invention lends itself particularly to the employment of such radiopaque filaments 13, as these can be retained readily in the ribs 11 or slots 12 without adverse effect to the overall flexibility of the member 9.

The invention claimed is:

1. A catheter and stent combination for insertion into the lumen of a human or animal body, the combination comprising:
   a catheter having a hollow body defined by walls, with proximal and distal ends, wherein at least one section of the walls of the hollow body in the distal region is corrugated and at least one section of the walls of the hollow body in the proximal region is smooth;
   an inflatable member disposed radially about the corrugated section; and
   a stent disposed about the inflatable member,
   wherein the corrugated section is an integral part of the distal wall of the catheter, and has a flexibility to that of another section of the hollow body.

2. A catheter according to claim 1, wherein the corrugation is provided by a series of circular indentations forming ribs therebetween.

3. A catheter according to claim 2, wherein slots are cut in the ribs that are formed to provide additional flexibility in the corrugations.

4. A catheter according to claim 1, wherein the corrugation is provided a single spiral indentation along the wall.

5. A catheter according to claim 1, wherein wire is inserted into the corrugated section to provide a region of increased radiopacity.

6. A catheter and stent combination for insertion into a lumen comprising:
   a catheter having a hollow body defined by walls, with proximal and distal ends, wherein at least one section of the walls of the hollow body in the distal region is corrugated and at least one section of the walls of the hollow body in the proximal region is smooth; and
   a stent, wherein the corrugated section is an integral part of the distal wall of the catheter, and has a flexibility to that of another section of the hollow body.

* * * * *